(12) United States Patent
Grode et al.

(10) Patent No.: US 6,277,556 B1
(45) Date of Patent: *Aug. 21, 2001

(54) CONTROLLING DONOR BLOOD CHARACTERISTICS

(75) Inventors: Gerald A. Grode, Vernon Hills; Mary A. Stewart, Mundelein, both of IL (US)

(73) Assignee: Baxter International Inc., Deerfield, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/213,214

(22) Filed: Dec. 17, 1998

Related U.S. Application Data (62) Division of application No. 08/970,249, filed on Nov. 13, 1997, now abandoned, which is a continuation of application No. 08/706,381, filed on Aug. 30, 1996, now abandoned, which is a continuation of application No. 08/357,812, filed on Dec. 16, 1994, now abandoned.

(51) Int. Cl.$^7$ ..................................... A01N 1/02
(52) U.S. Cl. .............................................. 435/2
(58) Field of Search ................................ 435/2

(56) References Cited

U.S. PATENT DOCUMENTS

| Re. 32,874 | 2/1989 | Rock et al. . |
| 4,390,619 | 6/1983 | Harmening-Pittiglio . |
| 4,405,719 | 9/1983 | Crews et al. . |
| 4,455,299 | 6/1984 | Grode . |
| 4,695,460 | 9/1987 | Holme . |
| 4,713,176 | 12/1987 | Schoendorfer et al. . |
| 4,764,463 | 8/1988 | Mason et al. . |
| 4,806,247 | 2/1989 | Schoendorfer et al. . |
| 4,828,976 | 5/1989 | Murphy . |
| 4,925,665 | 5/1990 | Murphy . |
| 4,931,002 | 6/1990 | Kornecki et al. . |
| 4,940,581 | 7/1990 | Mason et al. . |
| 4,961,928 | 10/1990 | Holme et al. . |
| 4,992,363 | 2/1991 | Murphy . |
| 4,994,367 | 2/1991 | Bode et al. . |
| 5,135,667 | 8/1992 | Schoendorfer . |
| 5,171,456 | 12/1992 | Hwang et al. . |
| 5,213,813 | 5/1993 | Kornecki et al. . |
| 5,234,808 | 8/1993 | Murphy . |
| 5,248,506 | 9/1993 | Holme et al. . |
| 5,494,590 * | 2/1996 | Smith et al. .................... 210/789 |

OTHER PUBLICATIONS

C.R. Valeri, et al.—Viability and function of red blood cell concentrates stored at 4° C for 35 days in CPDA–1, CPDA–2, or CPDA–3—Transfusion 22: 210–216 (1982).
B. Griffin, et al.—Studies on the Procurement of Blood Coagulation Factor VIII—Vox Sang 55: 9–13 (1988).
SIGMA Catalog, p. 263, entry 85–4 (1992).
C. Prowse, et al.—Studies on the Procurement of Blood Coagulation Factor VIII in vitro Studies on Blood Components Prepared in Half–Strength Citrate Anticoagulant—Vox Sang 52: 257–264 (1987).
Pert, J.H., et al., "Recent Advances in Preparation of Platelet Concentrates from ACD and CPD Blood"; XXIst Scientific Meeting of the Protein Foundation, Jul. 1967, pp. 119–126.
The Martindale, the Extrapharmacopoiea, 30th Ed., 1993, Composition ACD–A and CPD, p. 1456.
Bannai, M. et al., "The Effects of pH and Agitation on Platelet Preservation," Transfusion, vol. 25, No. 1, 1985, pp. 57–59.
Grode, D.R. et al., "Maintenance of pH During Platelet Storage," Transfusion, vol. 20, No. 5, Sep. 1980, p. 623.
C.F. Hogman, "Aspects of Platelet Storage," Transfusion Science, vol. 15, No. 4, 1994, pp. 351–355.

* cited by examiner

*Primary Examiner*—Sandra E. Saucer
(74) *Attorney, Agent, or Firm*—Robert M. Barrett; Bradford R. L. Price; Michael C. Mayo (57) ABSTRACT

A new citrate-based anticoagulant for donor whole blood provides good platelet yield and cell morphology at a significantly reduced risk of donor paresthesia during apheresis procedures. The primary citrate anticoagulant compositions include a citric acid to total citrate ratio greater than about 30%. The anticoagulants are mixed with whole blood to provide an anticoagulated blood mixture which contains a citric acid concentration of greater than about 5.0 mM, a total citrate concentration of less than about 20 mM, and an initial blood pH of less than about 6.75. The platelet rich products including PRP and PC prepared from blood collected in accordance with the invention exhibit better platelet yields and better platelet morphology on storage.

15 Claims, 5 Drawing Sheets

CONTROLLING DONOR BLOOD CHARACTERISTICS

CROSS-REFERENCE TO RELATED APPLICATIONS

This application is a Divisional of Ser. No. 08/970,249, filed Nov. 13, 1997, now abandoned, which was a Continuation of Ser. No.08/706,381, filed Aug. 30, 1996, now abandoned, which was in turn a Continuation of Ser. No.08/357,812, filed Dec. 16, 1994, also abandoned.

BACKGROUND OF THE INVENTION

The present invention generally relates to blood collection procedures and blood component separation methods. More particularly, it relates to new and improved methods of collecting blood into anticoagulant formulations designed to promote increased platelet yield and improved overall platelet morphology in platelet collection procedures.

Today there exists a number of automated donor hemopheresis systems for separation of blood, including whole blood into components or fractions. The systems are designed to collect one or more components, such as plasma, white cells, platelets and red cells, for further use or for disposal; to return certain components to the donor, who may be a patient; and/or to treat a component, for subsequent return to a donor. One such system is the Autopheresis-C® systems sold by Baxter Healthcare Corporation of Deerfield, Illinois, a wholly-owned subsidiary of the assignee of the present invention. That system utilizes a microprocessor-controlled instrument including automated processing programs, in conjunction with a disposable set.

The Autopheresis-C® device may, when disposable plasmapheresis set is installed therein, be used to collect plasma from whole blood drawn from a donor. A rotating membrane in a separation chamber of the disposable may in fact be wetted by an anticoagulant priming operation before blood is withdrawn from the donor, as shown in U.S. patent application Ser. No. 07/106,089, filed Oct. 7, 1987, entitled "Method for Wetting a Plasmapheresis Filter with Anticoagulant" and the corresponding PCT International Application Publication No. WO89/03229.

For the collection of platelets and plasma, the Autopheresis-C® system uses a single, two-stage set as disclosed in U.S. Pat. No. 4,851,126, entitled "Apparatus and Methods for Generating Platelet Concentrate". A set may include a rotating membrane separation chamber as set forth in U.S. patent application Ser. No. 73,378, and in corresponding Canadian Patent No. 1,261,765, as well as a centrifuge separator as set forth in U.S. Pat. Nos. 4,776,974 and 4,911,833, entitled "Closed Hemopheresis System and Method" and in International PCT Publication No. WO88/05332 entitled "Continuous Centrifugation System and Method for Directly Deriving Intermediate Density Material From a Suspension". If an anticoagulant source is pre-attached to the set, a biologically closed system, as medically defined, can be created.

A two-stage system enables the collection of blood from a donor for separation into platelet-rich plasma and packed red cells. The red cell suspension is returned to the donor by means of the same needle used to withdraw the whole blood. The platelet-rich plasma is collected in a container. The machine and set are disconnected from the donor. The collected platelet-rich plasma is then separated into plasma and platelet concentrate, utilizing a second stage of the biologically closed set.

Another automated closed system for separating blood fractions is the CS-3000® cell separator sold by Baxter Healthcare Corporation.

During withdrawal of blood and its subsequent treatment/separation, anticoagulant must be added in order to prevent clotting of the blood within the disposable tubing and separating set during the separation or collection of the blood. The conventional method of administering anticoagulant during automated apheresis procedures is to add anticoagulant during the step of withdrawal of the whole blood from the donor's vein. Anticoagulant from an anticoagulant container is administered through tubing to a location just downstream from the phlebotomy needle at a tubing junction, where the anticoagulant tubing line merges with the nonanticoagulated whole blood tubing line adjacent the phlebotomy needle in the donor.

There are at least four separate reasons for the addition of anticoagulant to the donor's blood during extracorporeal blood procedures. The first reason is to prevent the blood from clotting as it travels through the various tubes to the blood separator of the disposable set. The second reason is to prevent the blood from clotting as it is being separated. All separators require some exposure of blood to fluid shear stresses and these shear stresses can induce coagulation or agglomeration. The third reason is to prevent the separated cells from coagulation as they are being pumped through reinfusion filters and back to the donor. The fourth reason is to provide enough nutrients and sufficient pH buffering to permit storage of the separated blood component for a required duration of time.

The demand for anticoagulant in each of the four general steps identified above depends on the particular automated apheresis procedure. Some systems may induce significantly more shear stress during blood separation than other systems and, therefore, the upper limit demand for anticoagulant would be set by the separation step. Also, the separation technology used may have different stages wherein each separation stage may have its own, different demand level for the amount of anticoagulant in the blood.

Generally, the prior art has dealt with the issue of anticoagulant demand in automated procedures by adding to the whole blood, almost immediately upon its withdrawal from the donor, enough anticoagulant to meet the highest anticoagulant demand level during the entire withdrawal, separation, return and storage procedure. The anticoagulant is added adjacent the phlebotomy needle. The anticoagulant mixes with the whole blood upon being withdrawn from the donor. The prior art systems had been directed to adding as much anticoagulant as is necessary to prevent clotting with attention being paid to an upper limit dosage of anticoagulant, beyond which a so-called "citrate reaction" may occur in the donor upon return of an anticoagulated blood component to the donor.

Human blood collected by these apheresis procedures is anticoagulated in general practice by metering in a quantity of calcium ion chelating agent such as the sodium salts of citric acid. The ratio of human blood to citrate can be adjusted and controlled by various means and in general the ratio of blood to the citrate anticoagulant is made as large as possible to prevent the donor from experiencing any signs of paresthesia.

Reducing the quantity of anticoagulant administered to the patient on collection of whole blood is desirable for the patient donor but undesirable in terms of the ultimate storage stability and quantity of special blood components collected. More particularly to date, there is still a need to improve the total number of platelet cells recovered from these apheresis procedures and to improve the cell morphology on storage to provide better blood component products.

In the past, when using citrate-containing anticoagulants such as acid-citrate-dextrose (ACD-A) and citrate-phosphate-dextrose (CPD) type anticoagulants, it has generally been believed that the ratio of whole blood to anticoagulant should be maintained in the range of 25:1 to 6:1, and the final blood pH should be maintained at about 6.8 to about 7.2. Despite these earlier efforts, it is still desired to improve upon the quantity and quality of platelet concentrates by improving platelet collection conditions and procedures.

SUMMARY OF THE INVENTION

Unexpectedly in view of the foregoing, it has now been discovered that platelet cells collected at low pH are morphologically better maintained than those collected at higher more physiological pH. In addition, better yields can be achieved if whole blood is collected into a lower pH. The unexpectedly good morphology results are contrary to previous literature on platelet cell storage which indicates that as the pH of the platelets falls during storage, the morphologies and other cell indexes of viability tend to decline.

In accordance with the present invention, a new citrate-based primary anticoagulant preparation for donor whole blood is provided for addition to a human blood sample being collected for separation into human blood platelet products. The primary anticoagulant preparation comprises a calcium ion chelating agent-type of anticoagulant including citric acid and trisodium citrate wherein the ratio of citric acid to total citrate present is greater than about 30% by equivalent weight. The primary anticoagulant is added to whole blood so that upon collection a resulting collected blood/anticoagulant mixture is provided which contains a citric acid concentration of greater than about 5.0 mM, preferably at least about 7.0 mM or more, a total citrate concentration of less than about 20 mM, preferably from about 7.0 mM to about 18 mM, and an initial pH of less than about 6.75. When citrate-based anticoagulant agents are formulated in accordance with these guidelines and platelet-rich plasma and platelet concentrates are derived therefrom, it has been discovered that an improvement in terms of total cell counts per milliliter, that is cell yields, and cell morphology and cell quality are significantly improved.

In accordance with this invention, a new and improved method of providing human blood platelet products exhibiting improved platelet storage properties comprises the steps of collecting whole blood and mixing it with a primary anticoagulant formulation so as to form an anticoagulated blood mixture. The anticoagulant preparation includes citric acid and trisodium citrate wherein the ratio of citric acid to total citrate is greater than about 30%. The anticoagulated blood mixture in accordance with the method of the invention has a citric acid concentration of greater than about 5.0 mM, a total citrate concentration of less than about 20 mM and an initial pH of less than about 6.75. Thereafter, the anticoagulated blood mixture is separated into a human blood platelet preparation selected from the group consisting of platelet-rich plasma and platelet concentrates.

In accordance with this invention, better quality, better yield blood component products may be produced in a given collection procedure without undesirably increasing the amount of anticoagulant. This in turn reduces the risk of adverse reaction to anticoagulants for the patient donor.

Other advantages of the-present invention will become apparent from the following Detailed Description, Drawings and working Examples.

DETAILED DESCRIPTION OF THE PRESENTLY PREFERRED EMBODIMENTS

In accordance with the present invention, improved human blood platelet products may be prepared from whole blood in a collection procedure wherein whole blood is mixed with an anticoagulant formulation carefully designed to provide a relatively low amount of total citrate concentration, a relatively low blood pH level, and which is also added at a low anticoagulant to blood ratio, to provide improved platelet-rich plasma and platelet concentrate blood products obtained in better yield and having better overall cell morphologies on storage.

In accordance with this invention, major indicators as to the success of an apheresis procedure such as total cell counts and morphology are improved by carefully selecting the total citrate concentration, the acid concentration present, the blood pH and the ratio of blood to anticoagulant.

In accordance with the present invention, improved anticoagulant formulations are provided including citric acid and sodium citrate wherein the ratio of citric acid to the total citrate present is greater than about 30% up to and including 100%. When calculated on the basis of blood dilution, citric acid concentrations of about 7.0 mm and higher provided good results.

In accordance with this invention, improved platelet products are produced using the anticoagulant formulations of this invention, when the anticoagulants are mixed with collected blood so that the mixture contains a citric acid concentration of greater than about 5.0 mM, a total citrate concentration of less than about 20 mM, and an initial pH of less than about 6.75. Typically sufficient anticoagulant in solution is mixed with blood being collected to chelate calcium ions in the blood and prevent activation of the clotting mechanism.

In accordance with the present invention, the level of anticoagulant to blood ratio may be from about 1:6 to about 1:14 with good results being obtained without the need to increase the anticoagulant ratio.

The present invention is based on the unexpected discovery that collecting platelets at lower pH using higher citric acid ratios and lower ratios of total citrate provides platelet concentrates having increased cell numbers and improved cell morphology.

Other advantages provided by the present invention will be apparent from the following Examples.

EXAMPLES 1–19

In the following examples, blood was collected into various formulations of anticoagulating agent. The anticoagulated whole blood mixtures were processed first to form a platelet-rich plasma product (PRP) and then a final platelet concentrate (PC) was prepared using conventional centrifugal techniques and equipment. Each of these platelet-rich products PRP and PCs were then examined to determine the optimum formulation for the anticoagulant in terms of cell counts per milliliter (yields) and cell morphology (quality). In addition, the adequacy of the anticoagulation was assessed by determination of plasma fibrino peptide-A (FPA) which is an early marker of coagulation activation. Moreover, a number of other chemical/physical indexes were measured to assist in the overall evaluation of the product characteristics.

In the following experiments, data were collected to evaluate the effect on platelet yield and cell morphology provided by deliberately changing the citric acid/trisodium citrate ratios of a citrate buffer solution used to anticoagulate whole human blood. Citrate buffer solutions are anticoagulants whose base neutralizing strength is directly proportional to the amount of citric "acid" these solutions contain. Whole human blood is the "base" neutralized by the acidic citrate solution, thus the resultant blood pH falls in proportion to the amount of citric "acid" added. Total "citrate" (citric acid+trisodium citrate) is important for anticoagulant properties, but only the acid portion lowers blood pH.

The formulations tested and the results obtained are shown generally in Table 1 as follows:

TABLE 1

| EXAMPLE | Citric Acid (mM) | Sodium Citrate (mM) | Total Citrate (mM) | Blood Citric Acid (Mm) | Blood Sodium Citrate (mM) | Blood Total Citrate (mM) | Actual Whole Blood pH | NaCl (mg/dL) | Soln Osmolarity (OSM) |
|---|---|---|---|---|---|---|---|---|---|
| 1 | 0.670 | 26.830 | 27.500 | 0.109 | 4.368 | 4.477 | 7.264 | 650.0 | 275 |
| 2 | 0.670 | 68.080 | 68.750 | 0.109 | 11.083 | 11.192 | 7.245 | 314.1 | 283 |
| 3 | 0.670 | 109.330 | 110.000 | 0.109 | 17.798 | 17.907 | 7.221 | 0.0 | 294 |
| 4 | 11.700 | 15.800 | 27.500 | 1.905 | 2.572 | 4.477 | 7.096 | 699.8 | 276 |
| 5 | 11.700 | 43.300 | 55.000 | 1.905 | 7.049 | 8.953 | 7.093 | 472.7 | 280 |
| 6 | 11.700 | 70.800 | 82.500 | 1.905 | 11.526 | 13.430 | 7.075 | 251.9 | 282 |
| 7 | 19.439 | 90.561 | 110.000 | 3.164 | 14.742 | 17.907 | 6.972 | 56.0 | 287 |
| 8 | 27.500 | 0.000 | 27.500 | 4.477 | 0.000 | 4.477 | 6.868 | 817.9 | 269 |
| 9 | 29.181 | 25.819 | 55.000 | 4.750 | 4.203 | 8.953 | 6.833 | 562.9 | 281 |
| 10 | 29.181 | 53.319 | 82.500 | 4.750 | 8.680 | 13.430 | 6.836 | 317.2 | 278 |
| 11 | 34.350 | 75.650 | 110.000 | 5.592 | 12.315 | 17.907 | 6..739 | 199.5 | 310 |
| 12 | 43.463 | 0.000 | 43.463 | 7.075 | 0.000 | 7.075 | 6.672 | 766.3 | 280 |
| 13 | 43.463 | 33.537 | 77.000 | 7.075 | 5.459 | 12.535 | 6.669 | 515.0 | 304 |
| 14 | 43.463 | 66.537 | 110.000 | 7.075 | 10.832 | 17.907 | 6.654 | 267.7 | 318 |
| 15 | 0.670 | 26.830 | 27.500 | 0.109 | 4.368 | 4.477 | 7.264 | 650.0 | 275 |

| EXAMPLE | Solution pH | Actual Whole Blood pH | pCO$_2$ | pO$_2$ | Morph. Score (Morps cor) | Cell Count in PRP | Rel. Cell Count in PRP | Cell Count PC | Rel. Cell Count PC | HCT |
|---|---|---|---|---|---|---|---|---|---|---|
| 1 | 6.61 | 7.268 | 51.7 | 26 | 0 | 2.2E + 08 | 0.73 | 55230000 | 0.09 | 36 |
| 2 | 7.08 | 7.245 | 52.6 | 29 | 0 | 2.1E + 08 | 0.72 | 1.8E + 08 | 0.29 | 35 |
| 3 | 7.32 | 7.221 | 54.4 | 26 | 155 | 2.3E + 08 | 0.69 | 4.7E + 08 | 0.77 | 36 |
| 4 | 4.51 | 7.098 | 68.7 | 32 | 20 | 2.0E + 08 | 0.69 | 51229000 | 0.08 | 36 |
| 5 | 5.41 | 7.093 | 69.5 | 29 | 185 | 2.4E + 08 | 0.82 | 4.8E + 08 | 0.80 | 36 |
| 6 | 5.74 | 7.075 | 70.9 | 32 | 135 | 2.1E + 08 | 0.72 | 2.5E + 08 | 0.41 | 37 |
| 7 | 5.63 | 6.970 | 85.2 | 31 | 185 | 2.3E + 08 | 0.79 | 5.5E + 08 | 0.90 | 36 |
| 8 | 2.29 | 6.868 | 100.2 | 42 | 0 | 2.3E + 08 | 0.78 | 28825000 | 0.05 | 37 |
| 9 | 4.17 | 6.833 | 106.0 | 38 | 90 | 2.4E + 08 | 0.82 | 4.7E + 08 | 0.77 | 38 |
| 10 | 4.88 | 6.836 | 105.3 | 37 | 185 | 2.5E + 08 | 0.84 | 3.5E + 08 | 0.57 | 38 |
| 11 | 5.07 | 6.739 | 119.4 | 41 | 265 | 2.5E + 08 | 0.85 | 5.7E + 08 | 0.94 | 37 |
| 12 | 2.23 | 6.672 | 136.1 | 44 | 265 | 2.3E + 08 | 0.79 | 4.9E + 08 | 0.80 | 39 |
| 13 | 4.03 | 6.666 | 135.7 | 41 | 265 | 2.9E + 08 | 0.97 | 4.5E + 08 | 0.74 | 39 |
| 14 | 4.73 | 6.654 | 135.9 | 41 | 235 | 3.0E + 08 | 1.00 | 5.3E + 08 | 0.87 | 38 |
| 15 | 6.61 | 7.260 | 51.5 | 28 | 20 | 1.9E + 08 | 0.65 | 88400000 | 0.15 | 36 |

| EXAMPLE | Citric Acid (mM) | Sodium Citrate (mM) | Total Citrate (mM) | Blood Sodium Acid (mM) | Blood Blood Citrate (mM) | Blood Total Citrate (mM) | Actual Whole Blood pH | NaCl (mg/dL) | Soln. Osmol. (OSM) |
|---|---|---|---|---|---|---|---|---|---|
| 16 | 0.670 | 68.080 | 68.750 | 0.109 | 11.083 | 11.192 | 7.245 | 314.1 | 283 |
| 17 | 11.700 | 15.800 | 27.500 | 1.905 | 2.562 | 4.477 | 7.096 | 699.8 | 276 |

TABLE 1-continued

| | | | | | | | | | |
|---|---|---|---|---|---|---|---|---|---|
| 18 | 19.439 | 90.561 | 110.000 | 3.164 | 14.742 | 17.907 | 6.972 | 56.0 | 287 |
| 19 | 43.463 | 33.537 | 77.3000 | 7.075 | 5.459 | 12.535 | 6.669 | 515.0 | 300 |
| ACD 6.7 | 38.073 | 74.812 | 112.886 | 5.711 | 11.222 | 16.933 | 6.767 | | |
| 8 | | | | 4.759 | 9.352 | 14.111 | 6.847* | | |
| 9 | | | | 4.230 | 8.312 | 12.543 | 6.892* | | |
| 10 | | | | 3.807 | 7.481 | 11.289 | 6.928* | | |
| 11 | | | | 3.461 | 6.801 | 10.262 | 6.957* | | |
| 12 | | | | 3.173 | 6.234 | 9.407 | 6.982* | | |
| 13 | | | | 2.929 | 5.755 | 8.684 | 7.066* | | |
| 14 | | | | 2.720 | 5.344 | 8.063 | 7.020* | | |
| CPD 7.1 | 15.563 | 69.434 | 104.997 | 2.179 | 12.521 | 14.700 | 7.066* | | |
| 8 | | | | 1.945 | 11.179 | 13.125 | 7.086* | | |
| 9 | | | | 1.729 | 9.937 | 11.666 | 7.104* | | |
| 10 | | | | 1.556 | 8.943 | 10.500 | 7.119* | | |
| 11 | | | | 1.415 | 8.130 | 9.545 | 7.131* | | |
| 12 | | | | 1.297 | 7.453 | 8.750 | 7.141* | | |
| 13 | | | | 1.197 | 6.880 | 8.077 | 7.149* | | |
| 14 | | | | 1.112 | 6.388 | 7.500 | 7.157* | | |

| EXAMPLE | Solution pH | Actual Whole Blood pH | $pCO_2$ | $pO_2$ | Morph. Score (Morps cor) | Cell Count in PRP | Rel. Cell Count in PRP | Cell Count PC | Rel. Cell Count PC | HCT |
|---|---|---|---|---|---|---|---|---|---|---|
| 16 | 7.08 | 7.244 | 52.9 | 27 | 50 | 2.1E + 08 | 0.70 | 2.5E + 08 | 0.41 | 35 |
| 17 | 4.51 | 7.093 | 69.3 | 33 | 10 | 1.9E + 08 | 0.65 | 68289000 | 0.11 | 37 |
| 18 | 5.63 | 6.973 | 85.0 | 28 | 195 | 2.3E + 08 | 0.78 | 6.1E + 08 | 1.00 | 36 |
| 19 | 4.03 | 6.672 | 137.7 | 40 | 235 | 2.4E + 08 | 0.80 | 4.9E + 08 | 0.80 | 39 |

*= Predicted pH
Regression Output:
Constant: 7.250857
Std. Err of Y Est. 0.017085
R Squared 0.994573
No. of Observations 19
Degrees of Freedom 17
X Coefficient(s) −0.08476
Std. Err of Coef. 0.001518

As shown in Table 1, the experimental solutions contain a widely varied amount of "acid" concentrations of from about 0.67 mM to 43.46 mM combined with various concentrations of trisodium citrate from about 26.8 mM to 109.3 mM, providing total citrate concentrations of from about 27.5 mM to 110.0 mM. A total of 19 sample runs were made using the 14 distinct anticoagulant compositions of citric acids/trisodium citrate ratios with five trial replicates. Table 1 also contains information on the amount of sodium chloride (NaCl) added to each solution to insure isotonicity, as well as calculated resultant blood concentration of the citrate species using the tested ratio of blood/experimental solution of 6/1. Because of the neutralizing aspect of the addition, no actual citric acid exists in the final collected blood. However, the pH of the collected blood is reduced from a normal level of about 7.4 to the lower level shown in Table 1 under the heading actual WB pH. The right-hand portion of Table 1 provides data on each sample including specific values of resultant experimental solution osmolarity (OSM) and pH and then gives the resultant whole blood pH, $pCO_2$, $pO_2$, hematocrit (HCT).

In addition, isolated platelet characteristics including morphology (Morpscor 0-400) and platelet cell counts in the platelet-rich plasma (PRP) and platelet concentrate (PC) are also reported in Table 1. A "relative" cell count in both PRP and PC was calculated by dividing each specific result by the maximum results, giving the proportion for each result when compared to the maximum or best result. This was done because the total amount of whole blood used in each sample was only a fraction of a total normal blood unit and thus could not be processed in a standard fashion, so the proportion process standardizes the data.

Figure 1:
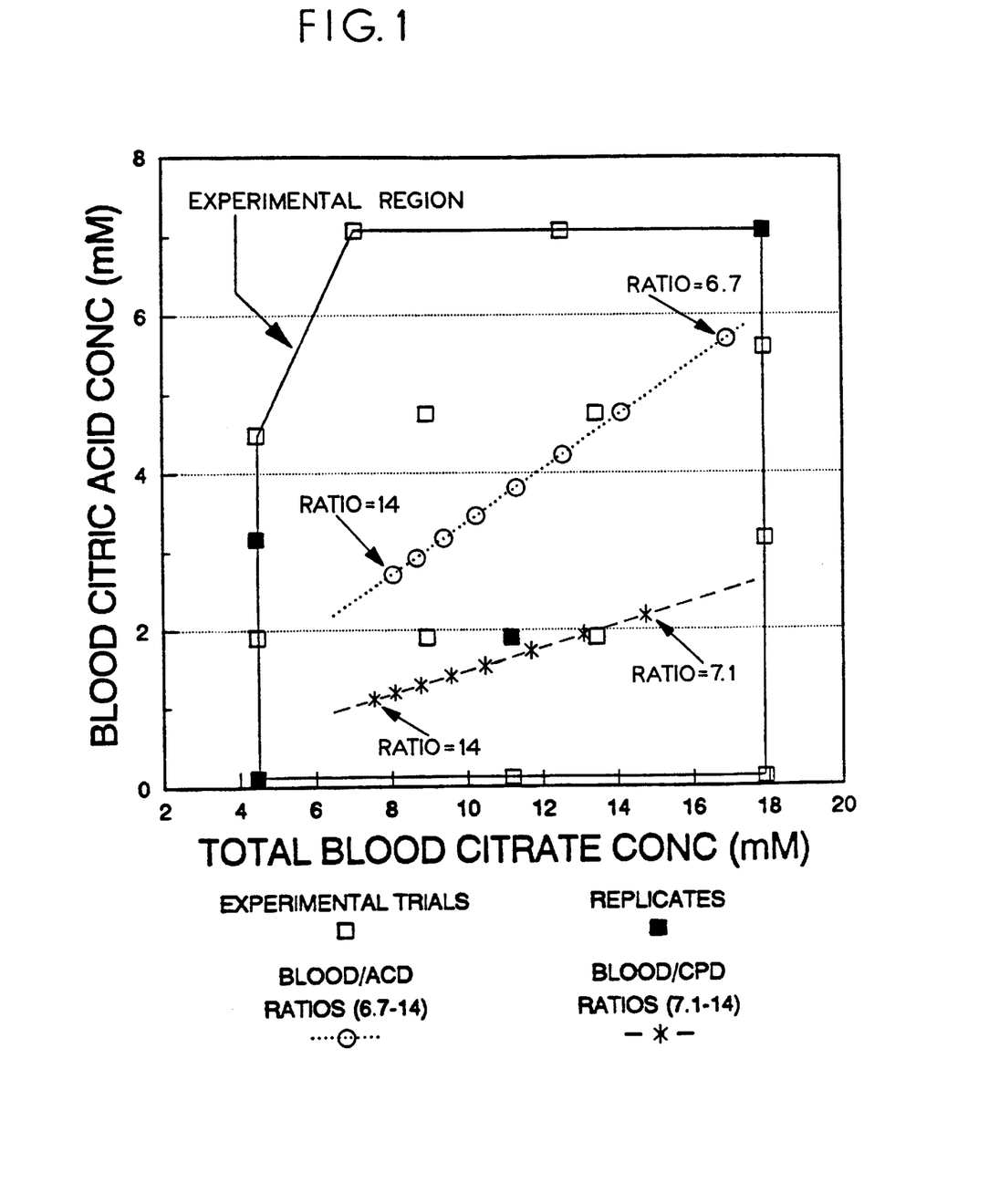
FIG. 1 is a graphical plot showing the blood citric acid concentration in millimoles as a function of total blood citrate concentration in millimoles resulting from the use of anticoagulant formulations comprising varying ratios of citric acid to trisodium citrate.

FIG. 1 provides a graphic display of the data presented in Table 1 showing the blood citric acid concentration on the y-axis and the blood total citrate concentration on the x-axis. Superimposed on this graph are calculated concentrations of the above x and y values for standard ACD (open circles) and CPD (asterisks) standard anticoagulants at blood/anticoagulant ratios of approximately 7/1 to 14/1. This was done to illustrate how the new and improved anticoagulants of the present invention, at the 6/1 ratio used, compare to various standard ratios currently used in the apheresis field for ACD anticoagulants. CPD values are also shown for comparative purposes and provide a good illustration of anticoagulants containing less citric acid as compared to ACD. As is shown in Table 1 and FIG. 1, the new and improved anticoagulant composition of this invention encompass and extend potential usable anticoagulant products over standard ACD types.

Figure 2:
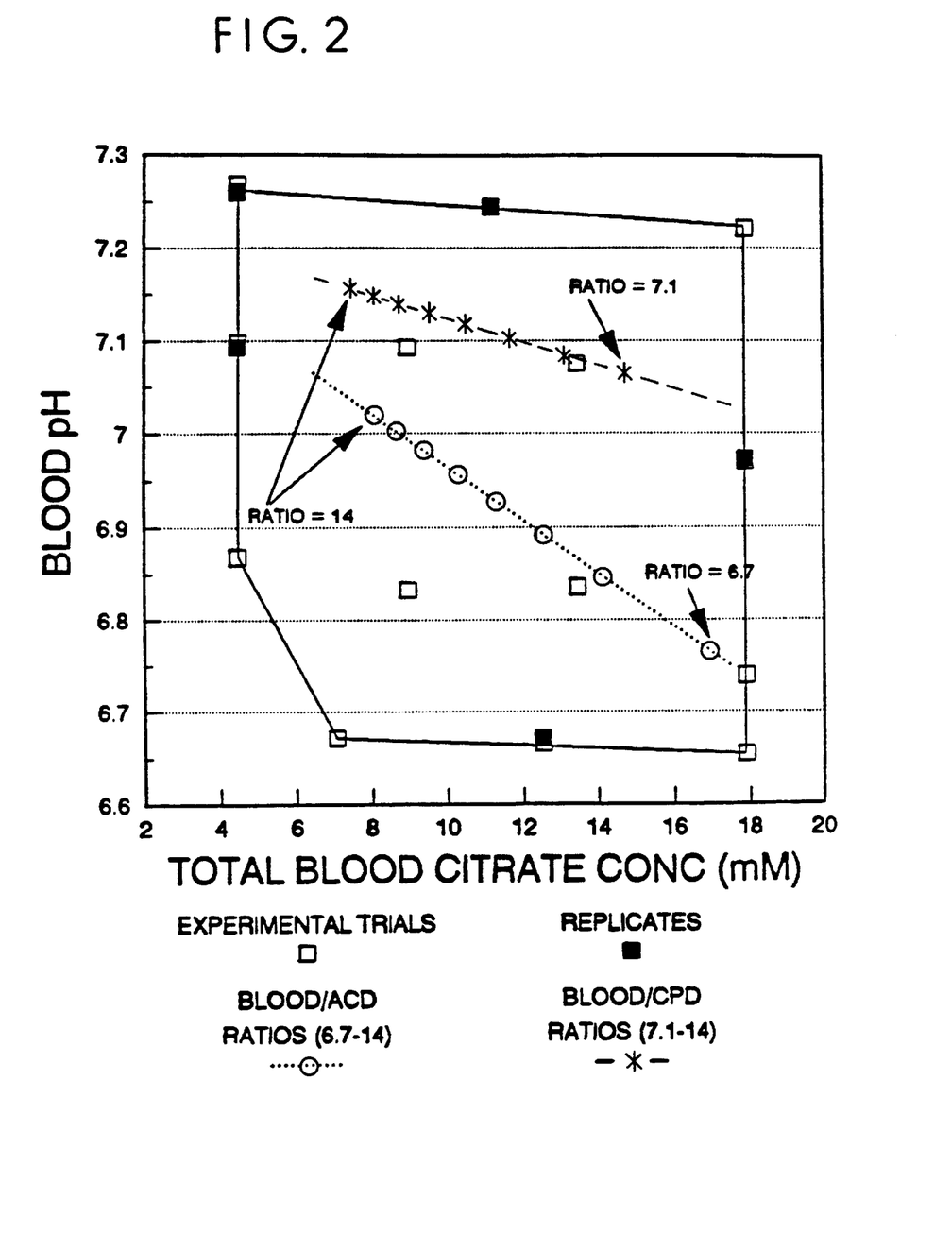
FIG. 2 is a graphical plot showing the blood pH achieved as a function of total blood citrate concentration shown for various ratios of blood to anticoagulant created upon collection.

FIG. 2 provides a graphical illustration of the pH of the resultant anticoagulated whole blood on the y-axis with the total blood citrate concentration shown on the x-axis. Again, the straight lines describing the result obtained with ACD and CPD standard anticoagulants are shown for comparison purposes. As shown in FIG. 2, blood pH of the experimental systems varied over a wide range of from about 6.0 to about 7.25, encompassing the standard anticoagulants under normal use.

An important and substantive point revealed by these data is that standard ACD anticoagulants employed under apheresis conditions are pushed to a ratio of 14:1 whole blood:anticoagulant levels to prevent donor paresthesia. In accordance with the present invention, the new and improved anticoagulant composition when used at a 6:1 whole blood:anticoagulant ratio and when citrate concentration was reduced provided equivalent and less citrate than standard anticoagulants delivered at much lower ratios, even at a 14:1 whole blood:ACD ratio.

Figure 6:
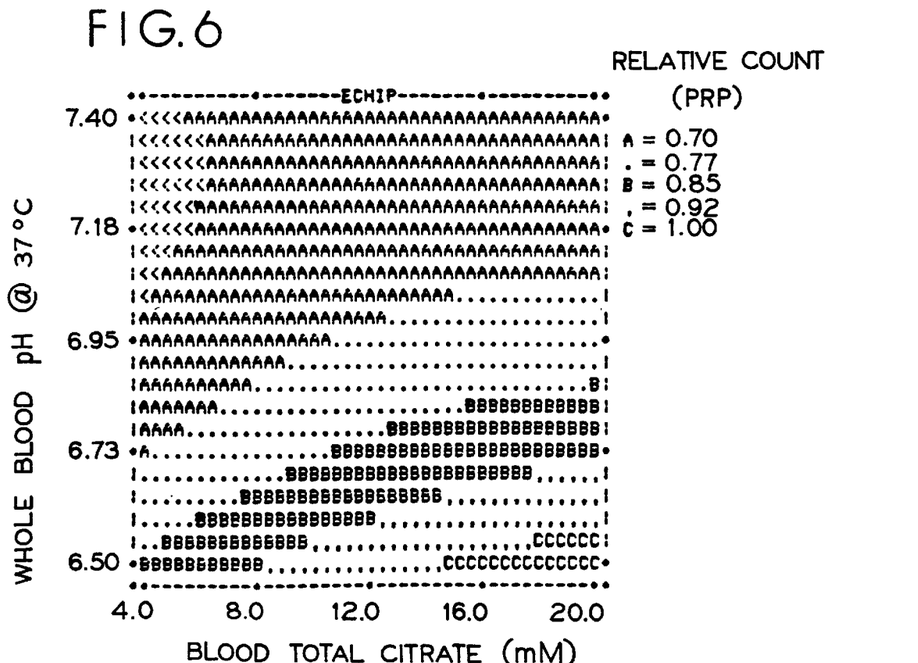
FIG. 6 is a contour plot graphically illustrating the effect of whole blood pH as a function of total blood citrate on relative cell counts collected in a platele-trich plasma product.
Figure 7:
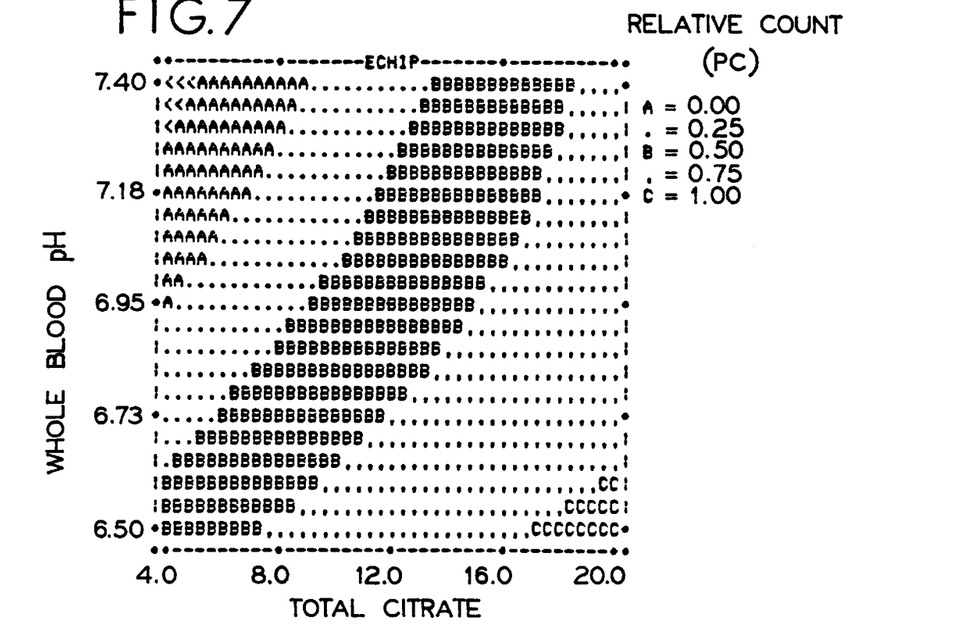
FIG. 7 is a contour plot graphically illustrating the effect of whole blood pH as a function of total citrate concentration on the relative cell counts in a platelet concentrate product.
Figure 8:
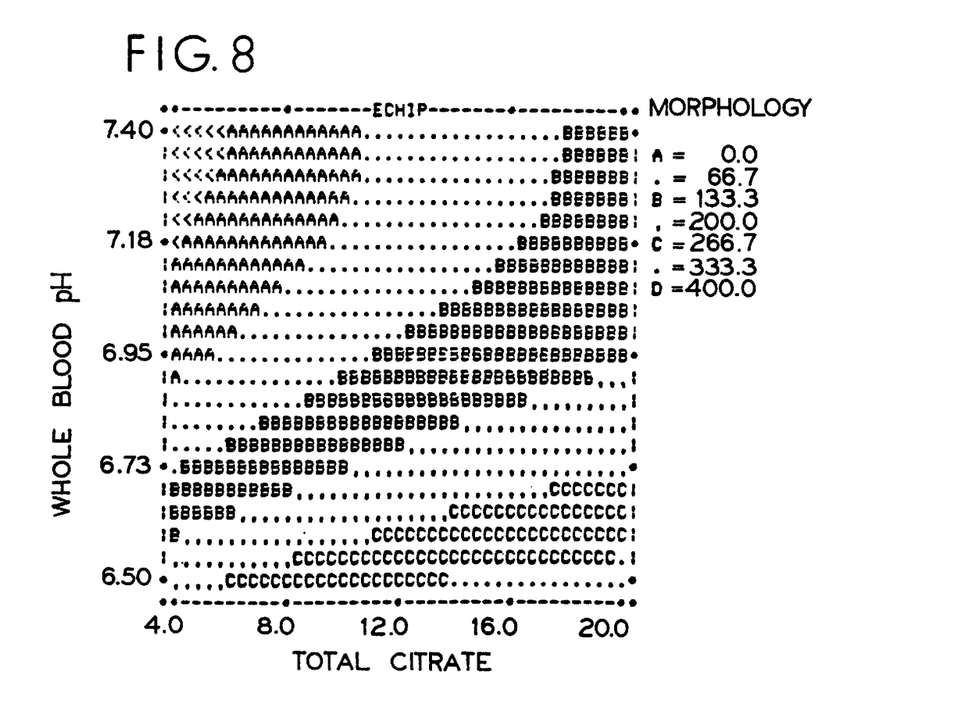
FIG. 8 is a contour plot graphically illustrating the effect of whole blood pH as a function of total citrate concentration on cell morphology collected in a platelet product.

The surprising results of these experiments are further illustrated in the contour plot shown in FIGS. 6–8. The surfaces described in these plots were obtained by a multivariate regression analysis using an ECHIP computer program on the data of Table 1. FIG. 6 shows the relative count of platelet cells obtained in the PRP. FIG. 7 shows the relative count of platelet cells in the PC. FIG. 8 shows the morphology of the collected platelet cells employing the Morpscor of 0 to 400, wherein 400 equals perfect discoid cells. The higher score, the better the result in each of these indices. The surface graphs are displayed using alpha characters, A–D, which describe the numerical trend going from low (A) to high (D).

FIGS. 6–7 describe "best yield" conditions. These occur when citrate levels are high and pH is low. This result was expected and it is likely due to a pH-associated deactivation of deleterious platelet activity. The unexpected result of improved morphology at low pH is illustrated by the contour plot shown in FIG. 8. As shown therein, good morphological characteristics were obtained at low pH over most of the evaluated citrate concentration range of from about 5.0 mM to 20 mM of citrate, with preferred C's occurring from about 7.0 mM to 18 mM citrate.

As indicated in Table 1, major indices such as cell count and morphology appear to change as a function of the specific anticoagulant formulation. A statistical analysis (multivariate regression of the data on blood citric acid concentration and total blood citrate concentration) was performed and the graphical representation of the resulting regression analysis for cell counts in PRP or PC and cell morphology are depicted in FIGS. 3, 4 and 5, respectively.

The individual effect of total citrate concentration and acid concentration were statistically significant on cell counts in both the PRP (citrate, p is less than 0.05; acid, p is less than 0.001) and PC (citrate, p is less than 0.001; acid, p is less than 0.05) and on cell morphology (citrate, p is less than 0.01; acid, p is less than 0.001).

Figure 3:
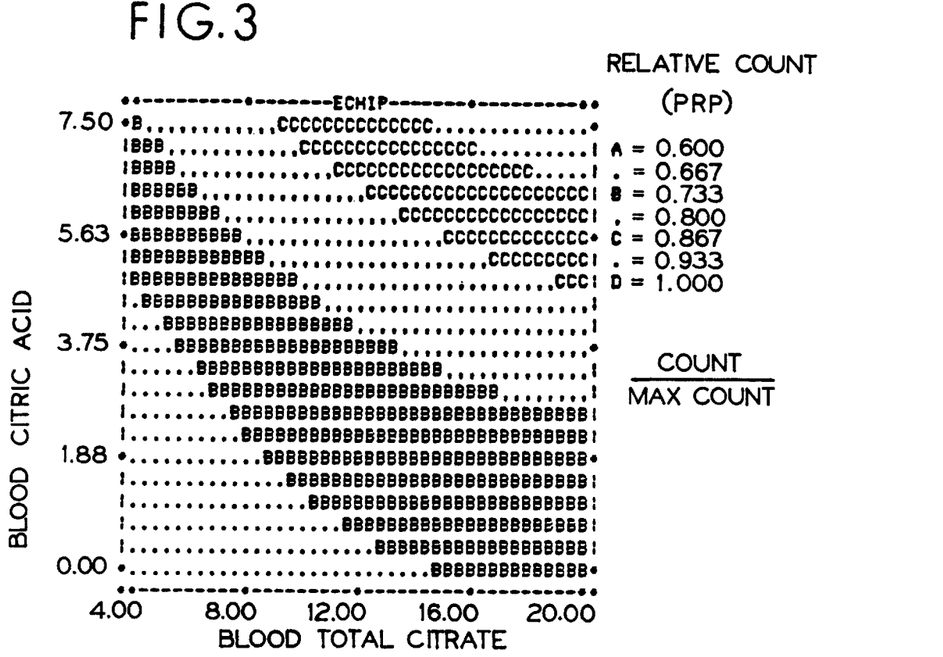
FIG. 3 is a contour plot graphically illustrating the effect of the ratio of blood citric acid concentration to blood total citrate concentration on the relative cell counts of platelets collected in a platelet-rich plasma product.
Figure 4:
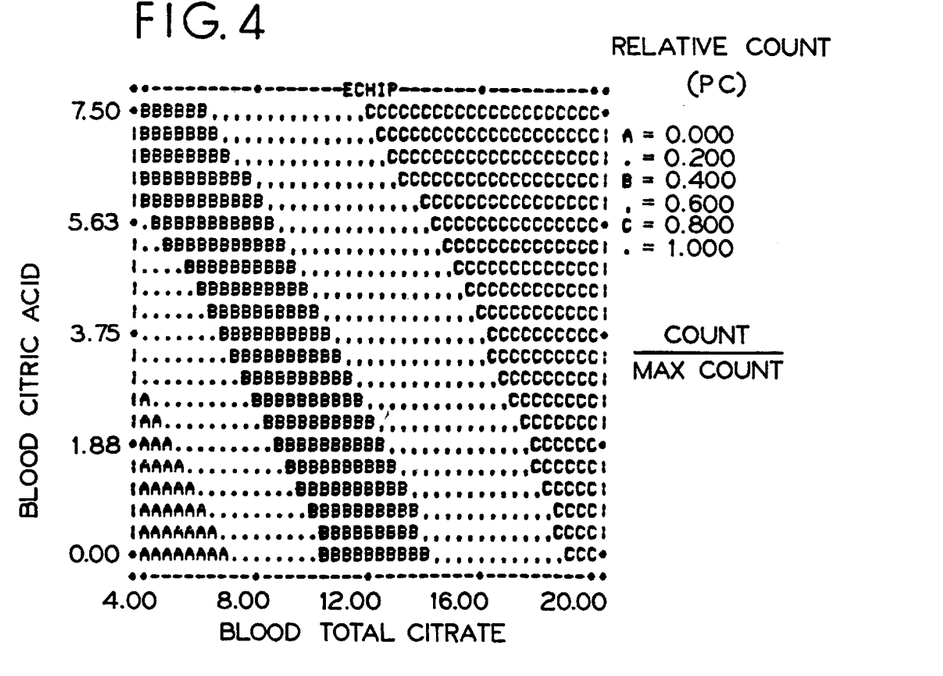
FIG. 4 is a contour plot graphically illustrating the effect of the ratio of blood citric acid concentration to blood total citrate concentration on the relative cell counts achieved in a platelet concentrate product.
Figure 5:
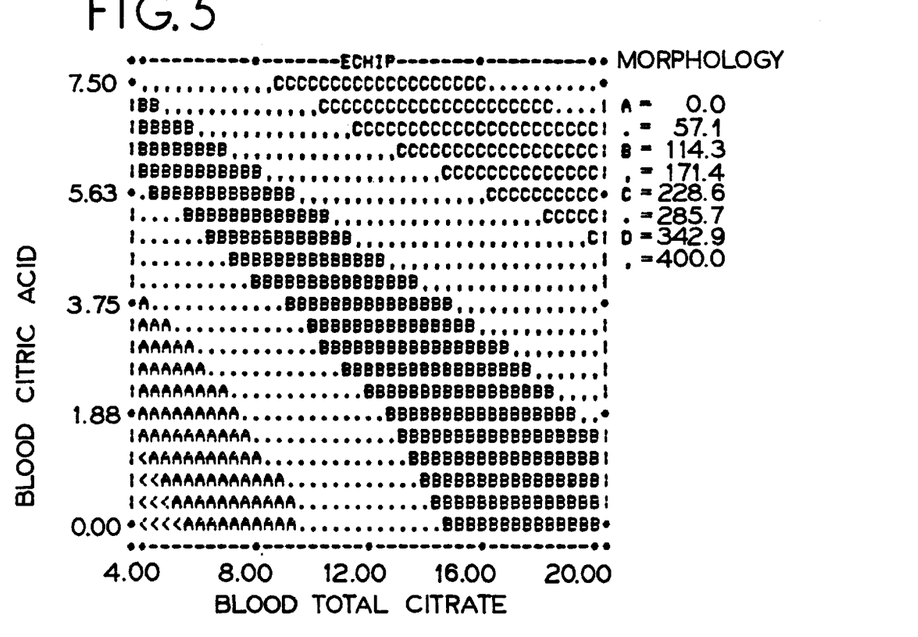
FIG. 5 is a contour plot graphically illustrating the effect of the ratio of blood citric acid concentration to blood total citrate concentration on the morphology of platelet cells collected in a platelet-rich plasma fraction.

As the contour plots shown in FIGS. 3, 4 and 5 indicate, cell counts are higher in both PRP or PC and morphologies of the PC cells are better as the citrate concentration increases or the acid component increases. Since the final blood pH is inversely correlated with the citric acid component of the anticoagulant ($R^2=0.995$, p is less than 0.0001), when cell counts (PRP or PC) and morphology are regressed on blood pH in total citrate, the contour plots depicted by FIGS. 6, 7 and 8 result. Statistical significance remains the same as above.

A graphical example of the observed blood pH at various ratios of blood to ACD-A is shown in the attached FIG. 2. Also shown are comparable changes using "CPD" anticoagulant. Experimental anticoagulants (Exp.-Anti) formulated in accordance with this invention with a variation to add fourteen different citric acid/trisodium citrate combination levels were evaluated and these are illustrated in FIG. 1. The appropriate combination for both ACD-A or CPD-type anticoagulants is also shown in the same figure.

FIG. 2 shows the resultant blood pH achieved when the specific combination of each of the above experimental anticoagulants is added to blood at a blood to experimental anticoagulant ratio of approximately 6:1. As indicated by FIG. 2, precise blood pH can be achieved at various total citrate concentrations by simply increasing the amount of citric acid (and reducing trisodium citric as shown in FIG. 1).

The unexpected conclusion from this study is that platelet cells collected at low pH are morphologically better maintained than those collected at higher, more physiological pH. In addition, better yields (higher cell counts) can be achieved at lower pH. The above was also true of total citrate concentration and this result was expected.

The unexpectedly good morphology results are contrary to the literature on platelet cell storage. That literature indicates that as the pH falls during storage, the morphologies and other cell indexes of viability tend to decline. This study contradicts that finding in that the lower the pH on collection, the better the overall morphology of the platelets.

These data support the general use of a new anticoagulant compositions based on reduced citrate concentrations containing relatively high concentrations of the "acid" component. Specifically, Examples 11–14 produced results leading to high morphology scores coupled with good yields. These Examples included a range of total blood citrate of 7 mM to 18 mM and each used citric acid concentrations of 7 mM when calculated on the basis of blood dilution. At the lowest citrate concentration of 7 mM this is equivalent to standard ACD delivered at high (greater than 14/1) blood/anticoagulant ratios. Accordingly, improved anticoagulant formulations are provided herein as compared to standard ACD and CPD types.

In accordance with this invention, any and all means available to those skilled in the art of formulating specific anticoagulant formulations may be used to enhance the combined effects of total citrate concentration and citric acid concentration to maintain a low blood pH while reducing (or raising) the total citrate concentration. Various mechanical means known to those skilled in the art may be used to separately meter in the appropriate quantities of the acid or salt of the citrate to formulate a final mixed anticoagulated blood product having the appropriate pH and ratios of anticoagulant to provide the improved platelet storage described herein.

Although the present invention has been described with reference to certain preferred embodiments, modifications or changes may be made therein by those skilled in this art without departing from the scope or spirit of the invention, as defined in the appended claims.

We claim:

1. A method of collecting human blood for preparing improved platelet preparations therefrom comprising the steps of:

withdrawing blood using an apheresis procedure from a donor through the use of a phlebotomy needle and a dedicated tubing line coupled to the phlebotomy needle;

introducing an anticoagulant during the apheresis procedure into the dedicated tubing line and thereby into the blood that is being collected, the anticoagulant mixing with the blood within the dedicated tubing line, wherein the anti-coagulant is a solution including citric acid and sodium citrate; and the anticoagulant and blood producing a resulting collected blood/anticoagulant mixture that contains a total calculated citrate concentration of 7.075 to 17.907 mM, calculated by adding the moles of citric acid to the moles of sodium citrate, and having an initial pH of 6.654 to 6.739.

2. The method of claim 1 wherein sufficient anticoagulant is introduced into the dedicated tubing line to achieve a ratio of whole blood: anticoagulant preparation of from about 6:1 to about 14:1.

3. The method of claim 1 wherein the anticoagulant preparation is introduced into the dedicated tubing line by allowing it to flow into the dedicated tubing line.

4. The method of claim 1 wherein the anticoagulant preparation is introduced into the dedicated tubing line by pumping it into the dedicated tubing line.

5. The method of claim 1 further comprising the step of subjecting the resulting collected blood/anticoagulant mixture to a blood separation procedure to provide a resultant platelet product selected from the group consisting of platelet-rich plasma products and platelet-concentrate products.

6. The method of claim 1 further comprising the step of subjecting the resulting collected blood/anticoagulant mixture to an automated blood separation procedure to provide a platelet concentrate product.

7. The method of claim 1 further comprising the step of subjecting the resulting collected blood/anticoagulant mixture to centrifugation separation processing to provide a platelet product selected from platelet-rich plasma and platelet-concentration products.

8. A method of human blood platelet preparation comprising:
collecting whole blood into a primary anticoagulant formulation to form an anticoagulated blood mixture at a ratio of 6:1 to 14:1, the anticoagulant preparation including citric acid and sodium citrate, the anticoagulated blood mixture having, a total citrate concentration, calculated by adding the moles of citric acid to the moles of sodium citrate, of 7.075 to 17.907 mM, and an initial pH of 6.654 to 6.739.

9. The method of claim 1 wherein the molar ratio of sodium citrate to citric acid in the anticoagulant prior to mixing was not more than 2.2.

10. The method of claim 4 wherein the molar ratio of sodium citrate to citric acid in the anticoagulant prior to mixing was not more than 2.2.

11. A composition comprising a mixture of blood and an anticoagulant consisting of sodium citrate and citric acid, the mixture having a pH of 6.654 to 6.739 wherein the total concentration of citrate in the mixture, calculated by adding the moles of citric acid to the moles of sodium citrate, is 7.075 to 17.907 mM, wherein the molar ratio of sodium citrate to citric acid combined to formulate the anticoagulant solution prior to mixing was equal to or less than 2.2.

12. A composition comprising a mixture of blood and an anticoagulant including sodium citrate and citric acid, the mixture having a pH of 6.654 to 6.739 and the total concentration of citrate in the mixture, calculated by adding the moles of citric acid to the moles of sodium citrate, is 7.075 to 17.907 mM.

13. The composition of claim 12 wherein the molar ratio of sodium citrate to citric acid combined to formulate the anticoagulant prior to mixing was 2.2 or less.

14. An intermediate blood product useful for making platelet preparations on further processing comprising a mixture of blood and an anticoagulant, the anticoagulant including sodium citrate and citric acid, the mixture having a pH of 6.654 to 6.739 and the total concentration of citrate in the mixture, calculated by adding the moles of citric acid to the moles of sodium citrate, is 7.075 to 17.907 mM.

15. The product of claim 14 wherein the molar ratio of sodium citrate to citric acid combined to formulate the anticoagulant prior to mixing was 2.2 or less.

* * * * *